United States Patent [19]

Marraccini et al.

[11] Patent Number: 5,013,472
[45] Date of Patent: May 7, 1991

[54] CHLOROTRIFLUOROETHYLENE TELOMERS

[75] Inventors: Antonio Marraccini, Novara; Gabriele Perego, Turin; Giovanni Guastalla, Novara, all of Italy

[73] Assignee: Ausimont S.R.L., Milan, Italy

[21] Appl. No.: 289,004

[22] Filed: Dec. 23, 1988

[30] Foreign Application Priority Data

Dec. 23, 1987 [IT] Italy .................. 23179 A/87

[51] Int. Cl.$^5$ .................. C10M 105/52; C10M 105/54
[52] U.S. Cl. .................. 252/78.1; 252/54; 252/58; 252/73; 568/676; 568/677; 568/683; 568/684; 568/614; 568/615; 570/134; 570/142
[58] Field of Search .................. 252/73, 75, 78.1, 54, 252/58; 568/676, 677, 683, 684, 614, 615; 570/134, 142

[56] References Cited

U.S. PATENT DOCUMENTS

| | | | |
|---|---|---|---|
| 3,076,765 | 2/1963 | West ........................ | 252/58 |
| 4,528,109 | 7/1985 | Fifolt et al. ................ | 252/58 |
| 4,533,762 | 8/1985 | Campbell et al. ........... | 568/677 |
| 4,577,044 | 3/1986 | Campbell et al. ........... | 568/677 |

FOREIGN PATENT DOCUMENTS 0269933 8/1988 European Pat. Off. .
2148286 5/1985 United Kingdom .

*Primary Examiner*—Paul Lieberman
*Assistant Examiner*—Christine A. Skane
*Attorney, Agent, or Firm*—Morgan & Finnegan

[57] ABSTRACT

New chlorotrifluoroethylene telomers and process for preparing them. Chlorotrifluoroethylene is reacted, at a temperature ranging from $-100°$ to $+40°$ C., with a fluoroxy compound of formula $R_x$—$CF_2OF$, wherein $R_x$ represents among others a perhalogenated alkyl radical containing from 1 to 10 carbon atoms. There are obtained telomer mixtures having, among others, the following formulae: $R_x$—$CF_2$—$O$—$(M)_n$—$F$; $R_x$—$CF_2$—$O$—$(M)_n$—$O$—$CF_2$—$R_x$; $R_x$—$(M)_n$—$F$; $R_x(M)_n$—$R_x$; $R_x$—$CF_2$—$O$—$(M)_n$—$R_x$ and $F$—$(M)_n$—$F$; wherein M is $CF_2$—$CFCL$ and "N" ranges from 2 to 20. Most of these telomers are new compounds.

33 Claims, No Drawings

CHLOROTRIFLUOROETHYLENE TELOMERS

DISCLOSURE OF THE INVENTION

The present invention relates to new telomers of chlorotrifluoroethylene. More particularly, it relates to new telomers prepared by reaction of chlorotrifluoroethylene with perhalofluoroxy compounds.

Chlorotrifluoroethylene telomers are particularly useful as hydraulic fluids. In general, they are prepared by reacting chlorotrifluoroethylene with chlorinated telogens, such as e.g., $CCl_4$ and $SO_2Cl_2$. The telomers so obtained contain polychlorinated end groups, for example, $-CFCl_2$ and $-CCl_3$, which, in applications or environments where high temperatures or oxidizing media are encountered, can be hydrolyzed or oxidized and thus give rise to corrosive acid groups.

Owing to the above-cited drawbacks, the telomers so obtained require a stabilizing fluorination treatment for the conversion of the polychlorinated end groups into groups having a higher fluorine content. This treatment is complex and expensive.

U.S. Pat. No. 4,577,044 describes a new type of chlorotrifluoroethylene telomers obtained by reacting same with $CF_3OF$. The following telomeric species are obtained: $F(CF_2-CFCl)_nF$; $CF_3O-(CF_2CFCl)_nF$; and $CF_3O-(CF_2CFCl)_n-OCF_3$, in which n usually ranges from 1 to 10 and the telomeric units $(CF_2-CFCl)$ are randomly distributed: namely, they can link to one another both in a head-to-head relationship and in a head-to-tail relationship.

In the telomeric products characterized, as these latter are, by not particularly high values of the degree of telomerization, it is assumed that the nature of the end groups and the type of bond (namely oxygen-carbon or carbon-carbon) by which these groups are bound to the monomeric units, may exert a considerable influence on the physical and chemical properties of the telomers, due in particular to different binding forces, different sizes of the groups and differences in the steric encumbrance or effect of said groups, and in the flexibility of the bond type (oxygen-carbon or carbon-carbon).

As a consequence thereof, the telomers of chlorotrifluoroethylene with $CF_3OF$ cannot exhibit a wide range of properties as they possess only the $CF_3O-$ and $F-$ end groups. Now, it is well known that an optimum property for one particular utilization of the chlorotrifluoroethylene telomers can constitute a handicap for some other utilization.

Thus, it is an object of the present invention to provide a process capable of providing chlorotrifluoroethylene telomers with inert end groups, both of the perhaloalkyl type (which bind therefore to the monomeric units by means of a carbon-carbon bond) and of the perhaloalkyoxy type, i.e., of the ether type (which bind therefore to the monomeric units by means of an oxygen-carbon bond).

Another object is that of providing a process which permits one to vary over a wide range both the distribution and nature of the end groups which are present on the telomers.

A further object is that of providing a process which permits one to vary over a wide range the F/Cl ratio in the telomers. This possibility has two important aspects. On the one hand, the obtainment of a higher F/Cl ratio, achieved by means of ether and non-ether perfluorinated end groups, modifies the physical and chemical properties of the telomers, thereby enabling one, for example to obtain lower pour point temperatures, lower combustion heat values, a lower surface tension, and a different variation of the viscosity as a function of temperature. On the other hand, for certain uses, a low F/Cl ratio, achieved through end groups containing Cl and F atoms, of the ether and non-ether types, imparts particular properties such as, for example, a decrease in the compressibility.

A still further object of the present invention is to provide a process which permits one, within certain limits to direct the telomerization reaction to the obtainment of telomeric species having a low degree of telomerization or, on the contrary, a higher degree of telomerization.

It is therefore apparent that the present invention provides a very flexible process capable of yielding a very broad range of products, with different physical and chemical characteristics, which permits one to meet various application requirements.

These and still other objects of the present invention are achieved by the herein-disclosed process for preparing chlorotrifluoroethylene telomers. This process is characterized in that chlorotrifluoroethylene is reacted, at a temperature ranging from $-100°$ to $+40°$ C., with a perhalofluoroxy compound of the formula $R_x-CF_2OF$, wherein $R_x$ is a perhalogenated alkyl radical, a perhaloalkyl monoether radical, or a perhaloalkyl polyether radical, either linear or branched, having from 1 to 10 carbon atoms, containing fluorine atoms or fluorine and chlorine atoms, but free from vicinal chlorine atoms and from $-CCl_3$ groups.

It is assumed that the reaction mechanism proceeds in part through the homolitic rupture of the O—F bond of the fluoroxy compound according to the scheme:

$$R_x-CF_2-OF \rightarrow R_x-CF_2-O\cdot + F\cdot$$

wherefore the radicals $R_x-CF_2-O\cdot$ and $F\cdot$ can act as telomerization starters and terminators. It is also assumed that the abovesaid radicals can also undergo further fragmentation and rearrangement reactions with the formation of other radical species which, in turn, can act as telomerization starters and terminators. In the case of radicals $R_x$ containing Cl atoms, it is furthermore supposed that one or more chlorine atoms may be replaced by fluorine atoms.

Starting from a perfluorofluoroxy compound, $R^1$ radicals deriving from $R_x$ do therefore form, in which $R_x$ having at least two carbon atoms has lost one or more carbon atoms and/or $R_x$ having at least three carbon atoms has undergone a re-arrangement. More usually, radical $R^1$ is an $R^2$ radical containing a lower number of carbon atoms with respect to $R_x$, wherefore when $R_x$ contains from 2 to 10 carbon atoms, $R^2$ contains from 1 to 9 carbon atoms. Starting from a perhalofluoroxy compound which contains chlorine, radical $R^3$ deriving from $R_x$ are formed, in which $R_x$ having at least two carbon atoms has lost one or more carbon atoms and/or $R_x$ at least 3 carbon atoms has undergone a re-arrangement, one or more chlorine atoms of $R_x$ having been replaced by fluorine atoms.

More commonly, radical $R^3$ is a $R^4$ radical containing a lower number of carbon atoms with respect to $R_x$ (wherefore when $R_x$ contains from 2 to 10 carbon atoms, $R^4$ contains from 1 to 9 carbon atoms) and in which one or more chlorine atoms have been replaced by fluorine atoms.

It has been discovered, in accordance with the present invention, that the telomerization product consists of a mixture of telomers having different end groups.

When starting from a perfluorofluoroxy compound, the telomers obtained are the following (in each telomer, monomeric unit $CF_2$—$CFCl$ is schematically represented by the letter M):

$$R_x-CF_2-O-(M)_n-F \quad (A)$$

wherein $R_x$ has the significance defined above and "n" ranges from 2 to 20.

$$R_x-CF_2\text{13 O}-(M)_n-O-CF_2-R_x \quad (B)$$

$$R_x-(M)_n-F \quad (C)$$

$$R_x-(M)_n-R_x \quad (D)$$

$$R_x-CF_2-O-(M)_n-R_x \quad (E)$$

$$R_x-O-(M)_n-F \quad (F)$$

$$R_x-O-(M)_n-O-CF_2-R_x \quad (G)$$

$$R_x-O-(M)_n-R_x \quad (H)$$

$$R_x-CF_2-(M)_n-F \quad (I)$$

$$R_x-CF_2-(M)_n-O-CF_2-R_x \quad (J)$$

$$R_x-CF_2-(M)_nR_x \quad (K)$$

$$R^1-O-(M)_n-OCF_2-R_x \quad (L)$$

wherein $R^1$ is a radical derived from $R_x$, in which $R_x$ having at least two carbon atoms has lost one or more carbon atoms and/or $R_x$ having at least three carbon atoms has undergone a re-arrangement.

$$R^1-O-(M)_n-R_x \quad (N)$$

$$R^1-(M)_n-F \quad (O)$$

$$CF_3-O-(M)_n-F \quad (P)$$

$$F-(M)_n-F \quad (Q)$$

The telomers from (A) to (E) and from (G) to (O) are new compounds. The telomers (F) are new when $R_x$ is different from —$CF_3$.

When starting from a perhalofluoroxy compound which contains chlorine, the telomers obtained are the following (in each of the telomers, monomeric unit $CF_2$—$CFCl$ is schematically represented by the letter (M): (A), (B), (C), (D), (E), (P) and (Q), indicated above $$R^3-O-(M)_n-OCF_2-R_x \quad (R)$$

wheren $R_x$ and n have the significance defined above while $R^3$ is a radical derived from $R_x$, in which $R_x$ having at least two carbon atoms has lost one or more carbon atoms and/or $R_x$ having at least three carbon atoms has undergone a rearrangement and one or more chlorine atoms of $R_x$ have been replaced by flourine atoms.

$$R^3-O-(M)_nR_x \quad (S)$$

$$R^3CF_2-O-(M)_n-F \quad (T)$$

$$R^3-CF_2-O-(M)_n-O-CF_2-R_x \quad (U)$$

$$R^3-CF_2-O-(M)_n-R_x \quad (V)$$

Telomers (R), (S), (T), (U) and (V) are new products. In the telomer chain $(M)_n$, monomeric units $CF_2$—$CFCl$ are linked at random, i.e., they follow one another both in a head-to-head arrangement and in a head-to-tail arrangement.

It has to be borne in mind that in the indicated telomer formulae, (M) may be either ($CF_2$—$CFCl$) or ($CFCl$—$CF_2$). So, to telomers $R_x-CF_2-O-(M)_n-F$ (A) there correspond two series of products represented by the formulae:

(b 1) $R_x-CF_2-O-(CF_2-CFCl)_n-F$ \quad (A$_1$)

in which end group $R_x-CF_2-O-$ is bound to group $CF_2$, while end group F is bound to group CFCl independently of the linkage of the intermediate monomeric units when n is higher than 2; and (b 2) $R_x-CF_2-O-(CFCl-CF_2)_n-F$ \quad (A$_2$)

in which end group $R_x-CF_2-O-$ is bound to group CFCl, while end group F is bound to group $CF_2$ independently of the linkage of the intermediate monomeric units when n is higher than 2.

In the telomer mixtures obtained from perfluorofluoroxy compounds or from perhalofluoroxy compounds containing chlorine, small amounts of telomers having a formula different from those indicated above may be present.

When $R_x$ is a perhaloalkylpolyether radical, it preferably contains two oxygen atoms.

Preferably, radical $R_x$ contains from 1 to 5 carbon atoms.

As already mentioned herein, when $R_x$ contains chlorine, it is free from vicinal chlorine atoms and from —$CCl_3$ groups; furthermore it is preferably free from —$CCl_2$— groups.

In the preferred products, n generally ranges from 2 to 10.

The telomer mixtures prepared by the process of the present invention are useful in particular as hydraulic fluids and as service fluids (operating fluids).

To carry out the reaction, a gaseous or liquid flow of perhalofluoroxy compound is generally fed to a reactor containing chlorotrifluoroethylene in the liquid state or dissolved in a solvent. When operating under pressure, the reaction may be conducted at a temperature which is higher than the chlorotrifluoroethylene boiling point (−27.9° C.). If it is carried out in a solution, a solvent of chlorotrifluoroethylene is used which is inert under the reaction conditions; in particular, a chlorofluorohydrocarbon, such as for example 1,2-dichlorotetra-fluoroethane, fluorotrichloromethane and dichlorodifluoromethane. Usually the chlorotrifluoroethylene content in the solution ranges from 20% to 80% by weight.

Generally, the fluoroxy compound is fed to the reactor as a gas stream. Preferably, the gaseous fluoroxy compound is diluted with a gas which is inert under the reaction conditions. Examples of inert diluting gases are nitrogen, argon, helium, and a gaseous chlorofluorohydrocarbon selected for example from among 1,2-dichlorotetrafluoroethane and dichlorodifluoromethane. Usually, the fluoroxy compound concentration in the gaseous mixture ranges from 5% to 80% by volume.

If the fluoroxy compound is fed in the liquid state to the reactor, it is subjected to mixing with a liquid which is inert under the reaction conditions; in particular, a chlorofluorohydrocarbon, for example 1,2-dichlorotetrafluoroethane, fluorotrichloromethane and dichlorodifluoromethane, or it is carried, in the form of an aerosol, by a gas which is inert under the reaction conditions, for example, nitrogen, argon or helium.

To the reactor containing a solvent of chlorotrifluoroethylene it is possible also to feed a gaseous or liquid fluoroxy compound flow, according to one of the feeding methods indicated hereinbefore, and, separately a gaseous or liquid chlorotrifluoroethylene flow; in this case, the chlorotrifluoroethylene is preferably fed in the liquid state.

The temperature at which the reaction is conducted ranges from $-100°$ to $+40°$ C. For each fluoroxy compound it is necessary to operate at a temperature which is at least equal to the threshold temperature of its reaction with chlorotrifluoroethylene, this temperature varying from telogen to telogen. Furthermore, as explained later on, the choice of the temperature value permits one to vary over a wide range both distribution and nature of the end groups which are present on the telomers, and to adjust, to a certain extent, the degree of telomerization. Preferably, operation is at temperatures ranging from $-30°$ to $80°$ C.

By the process of the present invention it is possible to direct the reaction in such as way as to obtain prevailingly the telomers of formulae:

$$R_x-CF_2-O-(M)_n-F \quad (A);$$

$$R_x-CF_2-O-(M)_n-O-CF_2-R_x \quad (B);$$

and $$F-(M)_n-F \quad (Q)$$

This result may be achieved by adopting conditions which reduce the amount of heat evolved in the reaction medium and which promote an effective dispersion thereof.

If the telomerization is effected by adduction of a telogen gaseous flow to the chlorotrifluoroethylene, either liquid or in solution, this result may be obtained by following one or more than one of the following procedures, or all of them:

(1) according to the first procedure, operation is in a lower temperature range, provided the temperatures are higher than the threshold temperature of the reaction;

(2) another procedure consists in precooling the telogen before it is fed. In such case, the telogen is fed in the gaseous state or in the liquid state; if it is introduced in the liquid state, feeding occurs according to the previously indicated procedures;

(3) a further procedure consists in decreasing the telogen flow rate or in increasing its dilution in the inert gas.

Another procedure which helps in obtaining the desired result consists in carrying out an effective stirring in the reactor.

Obviously, the lower temperature of the reaction medium and the more effective the stirring and the lower the precooling temperature of the telogen, the higher may be the telogen flow.

By operating according to these procedures and starting from $CF_3CF_2OF$, it is possible to obtain the above telomers (A), (B) and (Q) in amounts which may reach or exceed 90% by weight of the total of the reaction products.

Conversely, if operated at higher temperatures of the reaction medium and/or with higher telogen flow rates and with a less effective stirring, telomers different from (A) and (B) are obtained prevailingly. More precisely, in the case of perfluorinated telogens there are prevailingly obtained, for example, the following telomers:

$$R_x-(M)_n-F \quad (C)$$

$$R_x-(M)_n-R_x \quad (D)$$

$$R_x-CF_2-O-(M)_n-R_x \quad (E)$$

$$R_xO-(M)_n-F \quad (F)$$

$$R_x-CF_2-(M)_n-F \quad (I)$$

$$F-(M)_n-F \quad (Q)$$

In the case of chlorine-containing telogens there are obtained, for example, prevailingly the following telomers:

$$R_x-(M)_n-F \quad (C)$$

$$R_x-(M)_n-R_x \quad (D)$$

$$R_x-CF_2-O-(M)_n-R_x \quad (E)$$

$$F-(M)_n-F \quad (Q)$$

$$R^3-O-(M)_n-R_x \quad (S)$$

When operating according to the last mentioned procedures and when starting from $CClF_2-CF_2OF$, the abovesaid telomers are obtained in proportions which may reach or exceed 90% by weight of the total of the reaction products.

According to another feature of the present invention, under the conditions in which it is possible to direct the telomerization reaction prevailingly to the desired telomeric species, it is also possible, by reducing the amount of heat evolved in the reaction medium and by promoting an effective dispersion thereof, to direct, within certain limits, the degree of telomerization toward low values. This is attained with low telogen flow rates and with a lower temperature of the reaction medium and, optionally, by precooling the telogen. Another procedure which helps in obtaining this result consists in carrying out an effective stirring in the reactor. It is thus possible to obtain, for example up to 80% or above, of telomers having a value of "n" ranging from 3 to 6.

By operating under inverse conditions, i.e., with higher telogen flow rates and/or with a higher temperature of the reaction medium and, optionally, with a less intense stirring, the obtainment of telomers having higher values of "n" is promoted.

For each telogen it is possible, therefore, to direct the reaction to the obtainment prevailingly of telomers containing particular end groups, and to obtain, to a certain extent, a more or less low or a more or less high degree of telomerization. It is therefore evident that the process of the present invention permits one to obtain a wide range of products capable of meeting various application requirements.

Among the fluoroxy compounds utilizable in the process of the present invention, the following may be cited:
fluoroxy pentafluoroethane
1-fluoroxy heptafluoropropane
1-fluoroxy nonafluorobutane
1-fluoroxy 2-chlorotetrafluoroethane
1-fluoroxy 2,2'-dichlorotrifluoroethane
fluoroxy heptafluoroisopropane
fluoroxy nonafluoroisobutane
fluoroxy nonafluoro-ter.butane
1-fluoroxy-2-perfluoro n.propoxy-hexafluoropropane
1-fluoroxy-2-perfluoromethoxy-hexafluoropropane
1-fluoroxy-2-perfluoroethoxy-hexafluoropropane, and
1-fluoroxy-3-chlorohexafluoro n.propane.

When $CF_3CF_2OF$ is used as a telogen, the resulting telogen mixture is almost exclusively composed of the following species:

| | |
|---|---|
| $F(M)_nF$ | (Ia) |
| $F(M)_nOCF_2CF_3$ | (IIa) |
| $CF_3CF_2O(M)_n-OCF_2CF_3$ | (IIIa) |
| $CF_3(M)_n-F$ | (tm IVa) |
| $CF_3(M)_n-OCF_2CF_3$ | (Va) |
| $CF_3O(M)_n-OCF_2CF_3$ | (VIa) |
| $CF_3CF_2-(M)_n-F$ | (VIIa) |
| $CF_3CF_2(M)_n-OCF_2CF_3$ | (VIIIa) |
| $CF_3O(M)_nF$ | (IXa) |
| $CF_3-(M)_n-CF_3$ | (Xa) |

With the exception of species Ia and IXa, all the telomers thus obtained are new products.

By lowering the amount of heat evolved in the reaction medium and by favoring its effective dispersion according to the procedures specified hereinbefore, species Ia, IIa and IIIa may represent more than 85% of the obtained telomer mixture.

Conversely, by increasing the amount of heat evolved in the reaction medium, according to the procedures indicated hereinbefore, species Ia and IVa through IXa can represent more than 90% of the obtained telomer mixture.

When $CF_3-CF_2-CF_2OF$ is used as a telogen, the thus obtained telomer mix consists almost exclusively of the following species:

| | |
|---|---|
| $F(M)_nF$ | (Ia) |
| $F(M)_n-OCF_2CF_3$ | (IIb) |
| $F(M)_n-CF_2CF_3$ | (IIIb) |
| $CF_3CF_2CF_2-O(M)_n-OCF_2CF_2CF_3$ | (IVb) |
| $CF_3CF_2CF_2O-(M)_n-CF_2CF_3$ | (Vb) |
| $CF_3CF_2-(M)_n-CF_2CF_3$ | (VIb) |
| $CF_3CF_2CF_2O(M)_n-OCF_2CF_3$ | (VIIb) |
| $CF_3CF_2CF_2O(M)_n-OCF_3$ | (VIIIb) |
| $CF_3CF_2CF_2O(M)_n-CF_2CF_2CF_3$ | (IXb) |
| $CF_3CF_2CF_2(M)_n-F$ | (Xb) |
| $CF_3CF_2CF_2(M)_n-CF_2CF_3$ | (XIb) |
| $CF_3CF_2(M)_n-OCF_3$ | (XIIb) |
| $CF_3CF_2O(M)_n-F$ | (IIa) |
| $CF_3O(M)_n-F$ | (IXa) |
| $CF_3CF_2(M)_n-OCF_2CF_3$ | (VIIIa) |

Except for species Ia and IXa, all the telomers obtained are new products.

By lowering the amount of heat evolved in the reaction medium and by favoring an effective dispersion thereof according to the previously indicated procedures, species Ia and IIb through VIb may constitute more than 90% of the obtained telomer mixture.

When $ClCF_2-CF_2OF$ is used as a telogen, the thus obtained telomer mix consists almost exclusively of the following species:

| | |
|---|---|
| $F(M)_nF$ | (Ia) |
| $F(M)_n-OCF_2CF_2Cl$ | (IIc) |
| $ClCF_2-CF_2O-(M)_n-OCF_2CF_2Cl$ | (IIIc) |
| $ClCF_2-CF_2O-(M)_n-CF_2Cl$ | (IVc) |
| $F(M)_n-CF_2Cl$ | (Vc) |
| $CF_2Cl(M)_n-CF_2Cl$ | (VIc) |
| $ClCF_2CF_2O-(M)_n-OCF_3$ | (VIIc) |
| $ClCF_2CF_2O(M)_n-OCF_2CF_3$ | (VIIIc) |
| $CF_3CF_2O(M)_nCF_2Cl$ | (IXc) |
| $CF_3O(M)_n-CF_2Cl$ | (Xc) |
| $CF_3CF_2O(M)_nF$ | (IIa) |
| $CF_3O(M)_n-F$ | (IXa) |

With the exception of species Ia and IXa, all the telomers thus obtained are new products.

When lowering the amount of heat evolved in the reaction medium and promoting an effective dispersion thereof according to the procedures indicated hereinbefore, species Ia and IIc through VIc may represent more than 90% of the thus obtained telomer mixture.

The main advantages of the present invention may be summarized as follows:
(1) inert end groups are obtained which impart high characteristics of chemical and thermal stability to the telomers;
(2) it is possible to vary, over a wide range, both distribution and nature of the end groups which are present in the obtained telomeric species and, to a certain extent, the degree of telomerization thus obtaining a wide range of products having different physical and chemical properties which are suited to meet various different application requirements;
(3) it is possible to vary over a wide range the F/Cl ratio of the telomers obtained. Thus, it is possible to obtain products having a high F/Cl ratio and endowed with particular physical and chemical properties. Furthermore, it is possible to obtain telomers with a lower F/Cl ratio, which can impart particularly desired properties to the products such as, for example, a low compressibility.

EXAMPLES

The following examples are given merely to illustrate the invention and are not to be construed as a limitation thereof.

Example 1

A flow of 1.0 Nl/h of fluoroxypentafluoroethane and 3.0 Nl/h of $N_2$ was continuously bubbled into 450 g of liquid chlorotrifluoroethylene, cooled to $-55°$ C., in a 1-liter glass reactor equipped with a reflux cooler, a thermometer, and a mechanical stirrer.

After 4 hours and 30 minutes the reaction was stopped and the unreacted CTFE (chlorotrifluoroethylene) was distilled off.

Obtained were 71 g of products. By gas-chromatographic analysis, the composition was evaluated in "n" value, whereupon it was possible to calculate a yield of about 50% referred to $CF_3$—$CF_2OF$ corresponding to about 15.8 g of telomers per liter of gaseous telogen. The product was subjected to further analyses via gas-mass by means of a capillary column SE-52.

Moreover, $^{19}F$ N.M.R. spectra by means of a BRUKER apparatus AM 300 were carried out, dissolving the samples in $CDCl_3$.

From these tests it resulted that the product consisted of the telomeric species Ia to Xa, out of which species Ia to IIIa proved to form more than 85% of the mixture. Species IXa was present in an amount lower than 1%.

Gas-chromatographic analyses revealed that the terms having a value of "n" from 3 to 6 represented about 90% of the crude product. This crude product was then subjected to fractional distillation under reduced pressure. In this manner there were removed a head consisting of CTCE residues and of non-telomeric by-products, and a tail consisting of telomeric high-boiling products and of telomeric waxy products. The product so obtained was a colorless oil (designated as sample 1) where distribution of "n" values resulting from the gas-chromatographic analysis was as follows:

| Sample 1 | |
|---|---|
| Value of "n" | area % |
| 2 + volatile matters | 27.2 |
| 3 | 16.4 |
| 4 | 36.0 |
| 5 | 18.1 |
| 6 | 0.8 |

A second distillation of sample 1 under reduced pressure was then carried out in order to decrease the amount of telomers having an "n" value equal to 2. Obtained was sample 2 having the following distribution of "n" values:

| Sample 2 | |
|---|---|
| Value of "n" | area % |
| 2 | 2.3 |
| 3 | 25.4 |
| 4 | 45.9 |
| 5 | 22.1 |
| 6 | 4.3 |

In samples 1 and 2, the following physical and chemical properties were determined:
density according to method ISO R/758;
viscosity according to standard ASTM D445;
pour point according to standard ASTM D99;
vapor tension according to the method of the pressure transducer as is described in Journ. of Chem. and Eng. Data, vol. 13, No. 3, July 1969;
combustion heat according to standard ASTM D240;
unsaturation according to the method illustrated in the technical handbook by Halocarbon Product Corporation;
Bulk modulus by measuring the rate of the supersonic waves propagation.

The results obtained are recorded in the following Table 1.

TABLE 1

| Properties | Physical and Chemical Properties | Sample 1 | Sample 2 |
|---|---|---|---|
| Density | 20° C. | 1.8106 | 1.8522 |
| (g/ml) | 40° C. | 1.7722 | 1.8129 |
| Viscosity | −20° C. | — | 68.8 |
| (cSt) | −18° C. | 10.55 | — |
| | −15° C. | 9.34 | — |
| | −10° C. | 7.40 | 31.1 |
| | 0° C. | 4.95 | 16.4 |
| | 20° C. | 2.86 | 6.7 |
| | 40° C. | 1.99 | 3.4 |
| | 60° C. | 1.34 | 2.1 |
| | 80° C. | 0.99 | 1.4 |
| | 100° C. | 0.87 | 1.0 |
| | 120° C. | 0.71 | 0.8 |
| | 135° C. | 0.51 | 0.67 |
| Pour Point, °C. | | −78 | −58 |
| Vapor Tension at 121° C., Torr. | | 1030 | 270 |
| Combustion Heat cal/g | | 1410 | 1640 |
| Unsaturation (min.) | | 140 | 415 |
| Bulk Modulus | | — | $0.93083 \cdot 10^9$/Pa |

To be particularly noticed are the low values of pour point, combustion heat, and unsaturation.

Example 2

Following the procedures of Example 1, 1.0 Nl/h of $CH_3$—$CH_2OF$ and 4.0 Nl/h of nitrogen were bubbled into 450 g of liquid CTFE, at $-75°$ C., during 6 hours. After removal of the unreacted CTFE there were obtained 101 g of product with a yield of about 15.0 g of telomers per liter of gaseous $CF_3$—$CF_2OF$. The compounds from Ia to Xa were present. About 90% of the mixture was composed of the species from Ia to IIIa. The terms having a value of "n" ranging from 3 to 6 amounted to about 93% of the total.

Example 3

Following the procedures of Example 1, 2.0 Nl/h of $CF_3$—$CF_2OF$ and 4.0 Nl/h of $N_2$ were bubbled into 260 g of liquid CTFE, at $-40°$ C., for 3 hours and 30 minutes. After removal of the unreacted CTFE, there were obtained 63 g of product with a yield of about 9.0 g of telomers per liter of gaseous $CF_3$—$CF_2OF$. Compounds from Ia to Xa were present. The species from IVa to Xa represented about 90% of the mixture.

After the unreacted CTFE was distilled off, the distribution of the "n" values was found to be the following:

| Value of "n" | area % |
| --- | --- |
| 2 | not determined |
| 3 | 3.2 |
| 4 | 6.7 |
| 5 | 11.1 |
| 6 | 14.5 |
| 7 | 14.5 |
| 8 | 13.5 |
| 9 | 12.0 |
| 10 | 10.2 |
| 11 | 7.9 |
| 12 | 5.1 |
| $\geq 12$ | not determined |

Example 4

Following the procedures of Example 1, 1.0 Nl/h of $CF_3-CF_2OF$ and 3.0 Nl/h of $N_2$ were bubbled into 160 g of CTFE and were mixed with 160 g of $CF_2Cl-CF_2Cl$, at $-55°$ C., for 6 hours.

After the unreacted CTFE and the solvent were distilled off, 71 g of product were obtained, the yield being about 11.3 g of telomers per liter of gaseous $CF_3-CF_2OF$. Compounds Ia to Xa were present. About 90% of the mixture was composed of species Ia to IIIa. The terms having an "n" value ranging from 3 to 6 amounted to 76% of the total.

Example 5

Following the procedures of Example 1, 1.0 Nl/h of $CF_3-CF_2OF$ and 5.0 Nl/h of $N_2$ were bubbled into 200 g of CTFE and mixed with 200 g of $CFCl_3$, at $-75°$ C., for 14 hours. After the unreacted CTFE and the solvent were distilled off, there were obtained 180 g of product with a yield of about 12.9 g of telomers per liter of gaseous $CF_3-CF_2OF$. Compounds from Ia to Xa were present. Species Ia to IIIa represented about 90% of the mixture. The terms having an "n" value ranging from 3 to 6 corresponded to 66% of the total.

Example 6

Follwoing the procedures of Example 1, 1.0 Nl/h of $CF_3-CF_2-CF_2OF$ and 8.0 Nl/h of $N_2$ were bubbled into 260 g of CTFE, at $-50°$ C., for 8 hours. After the unreacted CTFE was distilled off, 72 g of product were obtained. A yield of about 9.0 g of telomers per liter of gaseous $CF_3-CF_2CF_2OF$ was calculated. The telomers from IIb to XIIb, Ia, IIa, VIIIa and IXa were present. The species Ia and from IIb to VIb represented about 90% of the mixture. Species IXa was present in an amount lower than 1%. The "n" values were distributed as follows:

| Value of "n" | area % |
| --- | --- |
| 2 + volatile matters | 44.7 |
| 3 | 20.9 |
| 4 | 14.7 |
| 5 | 7.9 |
| 6 | 5.1 |
| 7 | 3.2 |
| 8 | 2.3 |
| 9 | 1.1 |
| $\geq 10$ | Not determined |

Example 7

Following the procedures of Example 1, 1.0 Nl/h of $CF_3-CF_2-CF_2OF$ and 8.0 Nl/h of $N_2$ were bubbled into 260 g of CTFE and mixed with 260 g of $CF_2Cl-CF_2Cl$, at $-50°$ C., for 5 hours and 30 minutes. After having distilled off the unreacted CTFE and the solvent, 54 g of product were obtained. A yield of about 9.7 g of telomers per liter of gaseous $CF_3-CF_2-CF_2OF$ was calculated. Compounds from IIb to XIIb, Ia, IIa, IXa and VIIIa were present. More than 90% of the mixture was composed of species Ia and from IIb to VIb. The terms having "n" values from 3 to 6 amounted to about 60% of the total.

Example 8

Following the procedures of Example 1, 1.0 Nl/h of $CClF_2-CF_2OF$ and 5.0 Nl/h of $N_2$ were bubbled into 260 g of CTFE, at $-75°$ C., for 7 hours and 15 minutes. After distilling off of the unreacted CTFE, there were obtained 80 g of product with a yield of 11.0 g of telomers per liter of gaseous $CClF_2-CF_2OF$. Telomers from IIc to Xc, Ia, IIa and IXa were present. More that 90% of the mixture consisted of species Ia and from IIc to VIc. Species IXa was present in an amount less than 1%. The product was then subjected to fractional distillation at reduced pressure. Thereby there were removed a head prevailingly consisting of CTFE residues and a tail consisting of high-boiling products and of waxy products. Obtained was a colorless oil (designated as fraction 3), which had the following distribution of "n" values:

| Value of "n" | area % |
| --- | --- |
| 2 + volatile matters | 34.2 |
| 3 | 18.6 |
| 4 | 21.8 |
| 5 | 11.4 |
| 6 | 6.0 |
| 7 | 3.4 |
| $\geq 8$ | 2.2 |

In sample 3 there were determined the same physical and chemical properties as in Example 1.

The results are reported in the following Table 2:

TABLE 1

| Physical and Chemical Properties of Sample 3 | | |
| --- | --- | --- |
| Density | 20° C. | 1.8444 |
| (g/ml) | 40° C. | 1.8053 |
| Viscosity | $-20°$ C. | 28.6 |
| (cSt) | $-10°$ C. | 15.6 |
| | 0° C. | 9.7 |
| | 20° C. | 4.5 |
| | 40° C. | 3 |
| | 60° C. | 1.9 |
| | 80° C. | 1.2 |
| | 100° C. | 0.9 |
| | 120° C. | 0.74 |
| | 135° C. | 0.63 |
| Pour Point, °C. | | $-80$ |
| Vapor Tension at 121° C., Torr. | | 340 |
| Combustion Heat cal/g | | 1810 |
| Unsaturation (min.) | | 250 |
| Bulk Modulus | | $1.0263075 \cdot 10^9$/Pa |

It is to be noticed that the pour point value, the vapor tension, value, and the unsaturation value are particularly low. Also, the combustion heat value is low. From a comparison of the bulk modulus value with that of sample 2 (see Example 1), a higher value is observed, which is attributed to the presence of Cl in the end groups. Due to the high bulk modulus value, the sample is particularly suitable for use in applications where a low compressibility is required.

Example 9

Following the procedures of Example 1, 1.0 Nl/h of $CClF_2$—$CF_2OF$ and 5.0 Nl/h of N2 were bubbled into 130 g of CTFE mixed with 160 g of $CF_2Cl$—$CF_2Cl$, at $-74°$ C., for 9 hours. After having distilled off the unreacted CTFE and the solvent, there were obtained 59 g of product, with a yield of about 6.6 g of telomers per liter of gaseous $CClF_2$—$CF_2OF$. Compounds Ia, IXa and from IIc to Xc were present. More than 90% of the mixture was composed of species Ia and from IIc to VIc. About 40% of the mixture was composed of species Ia and from IIc to IVc. The terms having a value of "n" ranging from 3 to 6 hours were 58% of the total.

Example 10

Following the modalities of example 1, 1.0 Nl/h of $C_3F_7$—O—$CF(CF_3)$—$CF_2OF$ and 5.0 Nl/h of $N_2$ were bubbled in 250 g of CTFE at $-74°$ C. for 10 hours. After having distilled off the unreacted CTFE, there were obtained 58.5 g of product. They where obtained the telomers:

$F(M)_nF$ (Ia)

$CF_3O(M)_n$—F (IXa)

$CF_3O(M)_nOCF_3$ (3)

$C_3F_7O$—$CF(CF_3)$—$(M)_n$—F (4)

$C_3F_7O$—$CF(CF_3)CF_2O(M)_n$—F (5)

$C_3F_7O$—$CF(CF_3)$—$(M)_n$—$OCF_3$ (6)

$C_3F_7O$—$CF(CF_3)$—$CF_2O(M)_n$—$OCF_3$ (7)

$CF_3$—$CF_2$—$CF_2$—$CF(CF_3)$—$CF_2O(M)_n$—F (8)

$CF_3$—$CF_2$—$CF_2$—$CF(CF_3)$—$CF_2(M)_n$—$OCF_3$ (9)

$C_3F_7O$—$CF(CF_3)$—$(M)_n$—$CF(CF_3)$—$OC_3F_7$ (10)

$C_3F_7O$—$CF(CF_3)$—$(M)_n$—$OC_3F_6$—$OC_3F_7$ (11)

$C_3F_7O$—$C_3F_6O$—$(M)_n$13 $OC_3F_6$—$OC_3F_7$ (12)

$CF_3$—$CF_2$—$CF_2$—$CF(CF_3)$—$CF_2$—$(M)_n$—$CF(CF_3)$—$OC_3F_7$ (13)

$CF_3$—$CF_2$—$CF_2$—$CF(CF_3)$—$CF_2$—$(M)_n$—$OC_3F_6$—$OC_3F_7$ (14)

where "n" is comprised between 2 and 8.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

What is claimed is:

1. Chlorotrifluoroethylene telomers of formula:

$$R_x-CF_2-O-(M)_n-F \qquad (A)$$

in which $R_x$ is a perhalogenated alkyl radical, a perhaloalkylmonoether radical, or a perhaloalkylpolyether radical, wherein $R_x$ is either linear or branched, having 1 to 10 carbon atoms, containing fluorine atoms or fluorine atoms and chlorine atoms, but free from vicinal chlorine atoms and from —$CCl_3$ groups; M represents $CF_2$—CFCl and "n" ranges from 2 to 20.

2. Chlorotrifluoroethylene telomers of formula:

$$R_x-CF_2-O-(M)_n-O-CF_2-R_x \qquad (B)$$

in which $R_x$, M and "n" have the same significance as defined in claim 1.

3. Chlorotrifluoroethylene telomers of formula:

$$R_x-CF_2-O-(M)_n-R_x \qquad (E)$$

in which $R_x$, M and "n" have the same significance as defined in claim 1.

4. Chlorotrifluoroethylene telomers of formula:

$$R_x-O-(M)_n-F \qquad (F)$$

in which $R_x$, different from $CF_3$, M and "n" have the same significance as defined in claim 1.

5. Chlorotrifluoroethylene telomers of formula:

$$R_x-O-(M)_n-O-CF_2-R_x \qquad (G)$$

in which $R_x$, M and "n" have the same significance as defined in claim 1.

6. Chlorotrifluoroethylene telomers of formula:

$$R_x-O-(M)_n-R_x \qquad (H)$$

in which $R_x$, M and "n" have the same significance as defined in claim 1 and $R_x$ is different from $CF_3$.

7. Chlorotrifluoroethylene telomers of formula:

$$R_x-CF_2-(M)_n-O-CF_2-R_x \qquad (J)$$

in which $R_x$, M and "n" have the same significance as defined in claim 1.

8. Chlorotrifluoroethylene telomers of formula:

$$R^1-O-(M)_n-OCF_2-R_x \qquad (L)$$

in which $R_x$ is a perhalogenated alkyl radical, a perhaloalkylmonoether radical, or a perhaloalkyl polyether radical, wherein $R_x$ is either linear or branched, having 1 to 10 carbon atoms, containing fluorine atoms or fluorine atoms and chlorine atoms, but free from vicinal chlorine atoms and from —$CCl_3$ groups; M represents $CF_2$—CFCl; $R^1$ represents a radical derived from $R_x$ containing from 1 to b 9 carbon atoms; and "n" has a value ranging from 2 to 20.

9. Chlorotrifluoroethylene telomers of formula:

$$R^1-O-(M)_n-R_x \qquad (N)$$

in which $R_x$, M, $R^1$ and "n" have the same significance as defined in claim 8.

10. Chlorotrifluoroethylene telomers of formula:

$$R^3-O-(M)_n-OCF_2-R_x \text{ tm (R)}$$

in which $R_x$ represents a perhalogenated alkyl radical, a perhaloalkylmonoether radical, or a perhaloalkyl polyether radical, wherein $R_x$ is either linear or branched, having 1 to 10 carbon atoms, containing fluorine atoms and chlorine atoms, but being free from vicinal chlorine atoms and from —CCl₃ groups; M represents CF₂—CFCl; R³ is a radical derived from $R_x$ containing from 1 to 9 carbon atoms and one or more chlorine atoms of $R_x$ have been substituted by fluorine atoms, and "n" has a value ranging from 2 to 20.

11. Chlorotrifluoroethylene telomers of formula:

$$R^3—O—(M)_n—R_x \qquad (S)$$

in which $R_x$, M, R³ and "n" have the same significance as defined in claim 10.

12. Chlorotrifluoroethylene telomers of formula:

$$R^3—CF_2O—(M)_n—F \qquad (T)$$

in which M, R³ and "n" have the same significance as defined in claim 10.

13. Chlorotrifluoroethylene telomers of formula:

$$R^3—CF_2—O—(M)_n—O—CF_2—R_x \qquad (U)$$

wherein $R_x$, M, R³ and "n" have the same significance as defined in claim 10.

14. Chlorotrifluoroethylene telomers of formula:

$$R^3—CF_2—O—(M)_n—R_x \qquad (V)$$

wherein $R_x$, M, R³ and "n" have the same significance as defined in claim 10.

15. Telomers according to any one of claims 1 through 14, wherein radical $R_x$ contains 1 to 5 carbon atoms.

16. Telomers according to any one of claims 1 through 14, wherein radical $R_x$, when it contains fluorine atoms and chlorine atoms, is free from —CCl₂— groups.

17. Telomers according to any one of claims 1 through 14, wherein the value of "n" ranges from 2 to 10.

18. Chlorotrifluoroethylene telomer mixtures containing the species:

| | |
|---|---|
| $R_x—CF_2—O—(M)_n—F$ | (A) |
| $R_x—CF_2—O—(M)_n—O—CF_2—R_x$ | (B) |
| $R_x—(M)_n—F$ | (C) |
| $R_x—(M)_n—R_x$ | (D) |
| $R_x—CF_2—O—(M)_n—R_x$ | (E) |
| $R_x—O—(M)_n—F$ | (F) |
| $R_x—O—(M)_n—O—CF_2—R_x$ | (G) |
| $R_x—O—(M)_n—R_x$ | (H) |
| $R_x—CF_2—(M)_n—F$ | (I) |
| $R_x—CF_2—(M)_n—O—CF_2—R_x$ | (J) |
| $R_x—CF_2—(M)_n—R_x$ | (K) |
| $R^1—O—(M)_n—OCF_2—R_x$ | (L) |
| $R_1—O—(M)_n—R_x$ | (N) |
| $R^1—(M)_n—F$ | (O) |
| $CF_3—O—(M)_n—F$ | (P) |
| $F—(M)_n—F$ | (Q) | wherein $R_x$ represents a perhalogenated alkyl radical, a perhaloalkylmonoether radical, or a perhaloalkylpolyether radical, wherein $R_x$ is either linear or branched, having 1 to 10 carbon atoms, containing fluorine atoms or fluorine atoms and chlorine atoms, but free from vicinal chlorine atoms and from —CCl₃ groups; M represents CF₂—CFCl; R¹ represents a radical derived from $R_x$ containing from 1 to 9 carbon atoms, and "n" has a value ranging from 2 to 20.

19. Chlorotrifluoroethylene telomer mixtures containing the species:

| | |
|---|---|
| $R_x—CF_2—O—(M)_n—F$ | (A) |
| $R_x—CF_2—O—(M)_n—O—CF_2—R_x$ | (B) |
| $R_x—(M)_n—F$ | (C) |
| $R_x—(M)_n—R_x$ | (D) |
| $R_x—CF_2—O—(M)_n—R_x$ | (E) |
| $CF_3—O—(M)_n—F$ | (P) |
| $F—(M)_n—F$ | (Q) |
| $R^3—O—(M)_n—OCF_2—R_x$ | (R) |
| $R^3—O—(M)_n—R_x$ | (S) |
| $R^3—CF_2—O—(M)_n—F$ | (T) |
| $R^3—CF_3—O—(M)_n—O—CF_2—R_x$ | (U) |
| $R^3—CF_2—O—(M)_n—R_x$ | V) | in which $R_x$ represents a perhalogenated alkyl radical, a perhaloalkylmonoether radical, or a perhaloalkylpolyether radical, wherein $R_x$ is either linear or branched, having 1 to 10 carbon atoms, containing fluorine atoms and chlorine atoms, but free from vicinal chlorine atoms and from —CCl₃ groups; M represents CF₂—CFCl; R³ represents a radical derived from $R_x$ containing from 1 to 9 carbon atoms, and one or more chlorine atoms of $R_x$ have been substituted by fluorine atoms, and "n" has a value ranging from 2 to 20.

20. Chlorotrifluoroethylene telomer mixtures comprising the species:

| | |
|---|---|
| $R_x—CF_2—O—(M)_n—F;$ | (A) |
| $R_x—CF_2—O—(M)_n—O—CF_2—R_x$ | (B) |
| $F—(M)_n—F$ | (Q) | in which $R_x$, M and "n" have the same significance as defined in claim 18.

21. Chlorotrifluoroethylene telomer mixtures comprising the species:

| | |
|---|---|
| $R_x—(M)_n—F$ | (C) |
| $R_x—CF_2—O—(M)_n—R_x$ | (E) |
| $R_x—O—(M)_n—O—CF_2—R_x$ | (G) |
| $R_x—CF_2—(M)_n—F$ | (I) |

$$R_x-CF_2-(M)_n-O-CF_2-R_x \quad (J)$$

$$CF_3-O-(M)_n-F \quad (P)$$

$$F-(M)_n-F \quad (Q)$$

in which $R_x$, M and "n" have the same significance as defined in claim 18.

22. Chlorotrifluoroethylene telomer mixtures comprising the species:

$$R_x-(M)_n-F \quad (C)$$

$$R_x-(M)_n-R_x \quad (D)$$

$$R_x-CF_2-O-(M)_n-R_x \quad (E)$$

$$F-(M)_n-F \quad (Q)$$

$$R^3-O-(M)_n-R_x \quad (S)$$

in which $R_x$, M, $R^3$ and "n" have the same significance as defined in claim 19.

23. Mixtures of telomers according to any one of claims 18 to 22, wherein the radical $R_x$ contains 1 to 5 carbon atoms.

24. Mixtures of telomers according to any one of claims 18 to 22, wherein the radical $R_x$, when it contains fluorine atoms and chlorine atoms, is free from $-CCl_2$ groups.

25. Mixtures of telomers, according to any one of claims 18 to 22, wherein the value of "n" ranges from 2 to 10.

26. Chlorotrifluoroethylene telomers of formula $C_3F_7O-CF(CF_3)-(M)_n-F$ where "n" ranges from 2 to 8 and M represents $CF_2-CFCl$.

27. Chlorotrifluoroethylene telomers of formula $C_3F_7O-CF(CF_3)CF_2O(M)_n-F$ where "n" ranges from 2 to 8 and M represents $CF_2-CFCl$.

28. Chlorotrifluoroethylene telomers of formula $C_3F_7O-CF(CF_3)-(M)_n-OCF_3$ where "n" ranges from 2 to 8 and M represents $CF_2-CFCl$.

29. Chlorotrifluoroethylene telomers of formula $C_3F_7O-CF(CF_3)-CF_2O(M)_n-OCF_3$ where "n" ranges from 2 to 8 and M represents $CF_2-CFCl$.

30. Chlorotrifluoroethylene telomers of formula $C_3F_7O-CF(CF_3)-(M)_n-CF(CF_3)-OC_3F_7$ where "n" ranges from 2 to 8 and M represents $CF_2-CFCl$.

31. Chlorotrifluoroethylene telomers of formula $C_3F_7O-CF(CF_3)-(M)_n-OC_3F_6-OC_3F_7$ where "n" ranges from 2 to 8 and M represents $CH_2-CFCl$.

32. Chlorotrifluoroethylene telomers of formula $C_3F_7O-C_3F_6O-(M)_n-OC_3F_6-OC_3F_7$ where "n" ranges from 2 to 8 and M represents $CH_2-CFCl$.

33. Telomer mixtures consisting of $F(M)_nF$;

$CF_3O(M)_n-F$;

$CF_3O(M)_nOCF_3$;

$C_3F_7O-CF(CF_3)-(M)_n-F$ $C_3F_7O-CF(CF_3)CF_2O(M)_n-F$ $C_3F_7O-CF(CF_3)-(M)_n-OCF_3$ $C_3F_7O-CF(CF_3)-CF_2O(M)_n-OCF_3$ $CF_3-CF_2-CF_2-CF(CF_3)-CF_2-O(M)_n-F$ $CF_3-CF_2-CF_2-CF(CF_3)-CF_2(M)_n-OCF_3$ $C_3F_7O-CF(CF_3)-(M)_n-CF(CF_3)-OC_3F_7$ $C_3F_7O-CF(CF_3)-(M)_n-OC_3F_6-OC_3F_7$ $C_3F_7O-C_3F_6O-(M)_n-OC_3F_6-OC_3F_7$ $CF_3-CF_2-CF_2-CF(CF_3)-CF_2-(M)_n-CF(CF_3)-OC_3F_7$ $CF_3-CF_2-CF_2-CF(CF_3)-CF_2-(M)_n-OC_3F_6-OC_3F_7$ where "n" ranges from 2 to 8 and M represents $CF_2-CFCl$.

* * * * *